(12) United States Patent
Nguyen et al.

(10) Patent No.: US 7,975,531 B2
(45) Date of Patent: Jul. 12, 2011

(54) MICROFLUIDIC SENSOR FOR INTERFACIAL TENSION MEASUREMENT AND METHOD FOR MEASURING INTERFACIAL TENSION

(75) Inventors: Nam Trung Nguyen, Singapore (SG); Sumantri Lassemono, Singapore (SG); Franck Alexis Chollet, Singapore (SG); Chun Yang, Singapore (SG)

(73) Assignee: Nanyang Technological University, Singapore (SG)

( * ) Notice: Subject to any disclaimer, the term of this patent is extended or adjusted under 35 U.S.C. 154(b) by 314 days.

(21) Appl. No.: 11/886,380

(22) PCT Filed: Feb. 27, 2006

(86) PCT No.: PCT/SG2006/000038
§ 371 (c)(1),
(2), (4) Date: Sep. 14, 2007

(87) PCT Pub. No.: WO2006/098700
PCT Pub. Date: Sep. 21, 2006

(65) Prior Publication Data
US 2009/0019924 A1  Jan. 22, 2009

Related U.S. Application Data

(60) Provisional application No. 60/662,811, filed on Mar. 18, 2005.

(51) Int. Cl.
*G01N 13/02* (2006.01)

(52) U.S. Cl. ...... 73/64.52; 73/64.48; 356/244; 356/436; 356/601

(58) Field of Classification Search ...... 73/54.01–54.43, 73/64.48–64.52; 204/450–452; 356/344, 356/244, 436, 601
See application file for complete search history.

(56) References Cited

U.S. PATENT DOCUMENTS

| | | | |
|---|---|---|---|
| 5,699,157 A | | 12/1997 | Parce |
| 5,705,813 A | * | 1/1998 | Apffel et al. ............ 250/288 |
| 5,852,495 A | | 12/1998 | Parce |
| 5,972,187 A | * | 10/1999 | Parce et al. ............ 204/453 |
| 6,057,149 A | * | 5/2000 | Burns et al. ............ 435/287.2 |
| 6,130,098 A | * | 10/2000 | Handique et al. ........ 436/180 |

(Continued)

FOREIGN PATENT DOCUMENTS
AU    36634/97    2/1998
(Continued)

OTHER PUBLICATIONS

Nguyen et al., "Interfacial Tension Measurement with an Optofluidic Sensor", Sensors Journal, Institute of Electrical and Electronics Engineers, May 2007, pp. 692-697.*

(Continued)

*Primary Examiner* — David A. Rogers
(74) *Attorney, Agent, or Firm* — Seed Intellectual Property Law Group PLLC

(57) ABSTRACT

A microfluidic sensor is disclosed that has a first inlet channel for a first fluid, a second inlet channel for a second fluid, and a measurement channel intersecting with both first inlet channel and the second inlet channel. A signal source system is provided for receiving a signal from a signal emitter, as is a signal detection system for receiving the signal from the signal source system. The signal source system and the signal detection system are for recording physical characteristics of at least one of the droplets in the measurement channel. A corresponding method is also disclosed.

31 Claims, 12 Drawing Sheets

U.S. PATENT DOCUMENTS

| | | | |
|---|---|---|---|
| 6,233,048 B1 | 5/2001 | Parce | |
| 6,337,740 B1 | 1/2002 | Parce | |
| 6,590,653 B2 | 7/2003 | Parce | |
| 6,699,377 B2* | 3/2004 | Manz et al. | 204/453 |
| 6,949,176 B2 | 9/2005 | Vacca et al. | |
| 7,016,560 B2 | 3/2006 | Ticknor et al. | |
| 7,160,423 B2* | 1/2007 | Chien et al. | 204/453 |
| 7,259,849 B2* | 8/2007 | Ono et al. | 356/344 |
| 7,283,696 B2* | 10/2007 | Ticknor et al. | 385/14 |
| 7,355,699 B2* | 4/2008 | Gilbert et al. | 356/246 |
| 2002/0027075 A1* | 3/2002 | Manz et al. | 204/451 |
| 2002/0097398 A1 | 7/2002 | Parce | |
| 2003/0006140 A1 | 1/2003 | Vacca et al. | |
| 2003/0012483 A1 | 1/2003 | Ticknor et al. | |
| 2003/0017079 A1* | 1/2003 | Hahn et al. | 422/82.09 |
| 2003/0161572 A1 | 8/2003 | Johnck et al. | |
| 2005/0121324 A1* | 6/2005 | Park et al. | 204/451 |
| 2005/0133370 A1* | 6/2005 | Park et al. | 204/450 |
| 2005/0189224 A1 | 9/2005 | Parce | |
| 2006/0083473 A1 | 4/2006 | Ticknor et al. | |
| 2006/0272945 A1* | 12/2006 | Manz et al. | 204/451 |

FOREIGN PATENT DOCUMENTS

| | | |
|---|---|---|
| CA | 2257895 | 10/2005 |
| DE | 100 29 946 A1 | 12/2001 |
| EP | 0912886 | 9/2006 |
| WO | WO 98/02728 | 1/1998 |
| WO | WO 02/068821 | 9/2002 |
| WO | WO 02/069016 | 9/2002 |
| WO | WO 2006/098700 | 9/2006 |

OTHER PUBLICATIONS

Link, D. R. et al., "Geometrically Mediated Breakup of Drops in Microfluidic Devices", *Physical Review Letters*, vol. 92, No. 5, pp. 1-4, 2004.

International Search Report, PCT/SG2006/000038, 2 pages, May 25, 2006.

Office action dated Sep. 2, 2009 for German patent application No. 11 2006 000 642.8-52 (including English translation).

Olthuis et al., "Dynamic surface tension measured with an integrated sensor-actuator using electrolytically generated gas bubbles," *Sensors and Actuators B*, 49:126-132, 1998.

Thorsen et al., "Dynamic Pattern Formation in a Vesicle-Generating Microfluidic Device," *Physical Review Letters*, 86(18):4163-4166; 2001.

Drelich et al., "Measurement of Interfacial Tension in Fluid-Fluid Systems," *Encyclopedia of Surface and Colloid Science*, 3152-3166, 2002.

Nisisako et al., "Droplet formation in a microchannel network," *Lab Chip*, 2:24-26, 2002.

Dreyfus et al., "Ordered and Disordered Patterns in Two-Phase Flows in Microchannels," *Physical Review Letters*, 90(14):144505-1-144505-4, 2003.

Nisisako et al., "Novel microreactors for functional polymer beads," *Chemical Engineering Journal*, 101:23-29, 2004.

Truong et al., "A polymeric piezoelectric micropump based on lamination technology," *J. Micromech. Microeng.*, 14:632-638, 2004.

Bringer et al., "Microfluidic systems for chemical kinetics that rely on chaotic mixing in droplets," *Phil. Trans. R. Soc. Lond. A*, 362:1087-1104, 2004.

Zheng et al., "Formation of Arrayed Droplets by Soft Lithography and Two-Phase Fluid Flow, and Application in Protein Crystallization," *Adv. Mater.*, 16(15):1365-1368, 2004.

Okushima et al., "Controlled Production of Monodisperse Double Emulsions by Two-Step Droplet Breakup in Microfluidic Devices," *Langmuir*, 20:9905-9908, 2004.

Sun et al., "Low-pressure, high-temperature thermal bonding of polymeric microfluidic devices and their applications for electrophoretic separation," *J. Micromech. Microeng.*, 16:1681-1688, 2006.

* cited by examiner

INCREASE OF SURFACTANT CONCENTRATION
DECREASE OF SURFACE TENSION

MICROFLUIDIC SENSOR FOR INTERFACIAL TENSION MEASUREMENT AND METHOD FOR MEASURING INTERFACIAL TENSION

FIELD OF THE INVENTION

This invention relates to microfluidic sensor for interfacial tension measurement and method for measuring interfacial tension and relates particularly, through not exclusively, a microfluidic device and methods for quick measurements of interfacial surface tension with a small quantity of a sample liquid.

BACKGROUND TO THE INVENTION

As shown in FIG. 1, known measurement methods of interfacial tension can be placed in five groups:
- direct measurement using microbalance;
- measurement of capillary pressure;
- analysis of capillary gravity forces;
- gravity distorted drop; and
- reinforced distortion of drop.

In the first method, surface tension is measured directly by a force sensor. Such systems use a plate or a ring of platinum-iridium alloy or platinum. The plates and rings have of standard dimensions, thus no calibration is required. In the second method, surface tension is proportional to capillary pressure, which can be measured directly with a pressure sensor. The third method measures gravity rise or size of a droplet after detachment. In the fourth method, the shape of the droplet is distorted by surface tension and gravity. Measuring the geometry of a pendant drop allows the determination of surface tension. For this measurement method, a CCD camera and computer evaluation is needed. The spinning drop technique evaluates the distortion of a drop and needs a CCD camera.

Besides these techniques, there is interest in interfacial tension measurement of small samples. The study of interfaces of very small particles and in finely dispersed systems is micro tensiometry. The main application fields of micro tensiometry are criminology, biology and pharmaceutical micro reactors. The two methods currently known for micro tensiometry are:
(a) micropipette technique; and
(b) atomic force microscopy.
These are shown in FIG. 2.

In the micropipette technique of FIG. 2(a), a droplet is first captured at the tip of a micropipette. Utilizing the radian of curvature on both sides of the droplet as shown in FIG. 2(a)A, the surface tension can be calculated. This technique requires a microscope and an image recording system. The second approach of direct force measurement as shown in FIG. 2(a)B. A force sensor is again required.

A miniaturized version of the direct measurement method depicted in FIG. 1 is the use of atomic force microscopy to determine extremely small forces (FIG. 2(b)). The deflection of the micro cantilever is measured with a laser beam. Forces of the order of 1 pN can be measured. It has been proposed to use bubble generation and surface tension evaluation. The bubble is generated by electrolysis and detected electronically. The frequency of bubble formation is a measure surfactant concentration. A multi-well plate reader may be modified to evaluate surface tension. This technique utilizes the radius of curvature of the liquid surface acting as a fluidic lens and requires a camera system and an expensive commercial plate reader system.

All micro tensiometry techniques above require individual handling of a single droplet. As such, evaporation is a problem. Furthermore, the measurement is expensive and requires dedicated equipment. The bubble generation system is limited by the gas/liquid system of an aqueous sample.

It would be of advantage to be able to measure interfacial tension of micro droplets and bubbles in a simple configuration utilizing microfluidic technology. This should enable:
- a small sample size, higher accuracy, and faster results;
- interfacial tensions of all immiscible systems (both liquid/liquid and gas/liquid);
- lower cost and easier handling
- be suitable for hand-held systems and portable field measurements; and
- an integrated "lab-on-chip" device with a microchannel and optical wave guides is possible.

SUMMARY OF THE INVENTION

In accordance with a first preferred embodiment there is provided a microfluidic sensor comprising:
(a) a first inlet channel for a first fluid;
(b) a second inlet channel for a second fluid;
(c) a measurement channel intersecting with both first inlet channel and the second inlet channel;
(d) a signal source system for receiving a signal from a signal emitter;
(e) a signal detection system for receiving the signal from the signal source system;
(f) the signal source system and the signal detection system being for recording physical characteristics of at least one of the droplets in the measurement channel.

According to a second preferred aspect there is provided a method for measuring physical characteristics of at least one droplet of a first fluid in a measurement channel of a microfluidic sensor, the method comprising:
(a) forcing a first fluid along a first inlet and into the measurement channel;
(b) forcing a second fluid along a second inlet and into the measurement channel to form the at least one droplet;
(c) using a signal source system to provide a source signal and a signal detection system to detect the source signal;
(d) recording physical characteristics of the at least one droplet in the measurement channel by using the signal source system and the signal detection system.

The first inlet channel, the second inlet channel and the measurement channel may be in a substrate. The first fluid may be air and the droplets may be air bubbles.

The signal source system may be a source wave guide, the signal may be light, and signal detection system may be a detection wave guide. The source wave guide may be a source optical fibre, and the detection wave guide may be a detection optical fibre. The source wave guide and the detection waive guide may be in the substrate.

The signal source system and the signal detection system may be axially aligned on opposite sides of and intersect with the measurement channel. The signal source system and the signal detection system may be substantially identical.

The substrate may be transparent. The signal source system may be a light emitter and the signal detection system may be an optical sensor; one of the light emitter and the optical sensor may be above the measurement channel, and the other of the light emitter and the optical sensor may be below the measurement channel.

The physical characteristics may be at least one of: droplet length, droplet size, advancing edge shape, receeding edge shape, contact angle of the at least one droplet with the measurement channel, velocity of movement of the at least one droplet in the measurement channel, speed of movement of the at least one droplet in the measurement channel, and frequency of droplet formation.

The signal emitter may be a laser emitter, and the signal detector may be an optical sensor. The microfluidic sensor may further comprise a first fluid reservoir operatively connected to the first inlet channel, a second fluid reservoir operatively connected to the second inlet channel, and a waster reservoir operatively connected to an outlet end of the measurement channel.

The microfluidic sensor may further comprise a first pump operatively connected to the first fluid reservoir for forcing the first fluid into the first inlet channel and the measurement channel; and a second pump operatively connected to the second fluid reservoir for forcing the second fluid into the second fluid outlet and the measurement channel.

According to a third preferred aspect there is provided a tensiometer module comprising a receptor for a microfluidic sensor as described above, the receptor comprising electrical and optical connections for the microfluidic sensor and one of: a microcontroller and a digital signal processor.

According to a fourth preferred aspect there is provided computing apparatus comprising a tensiometer module as described above, and a screen. The tensiometer module may be removable.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

Figure 1:
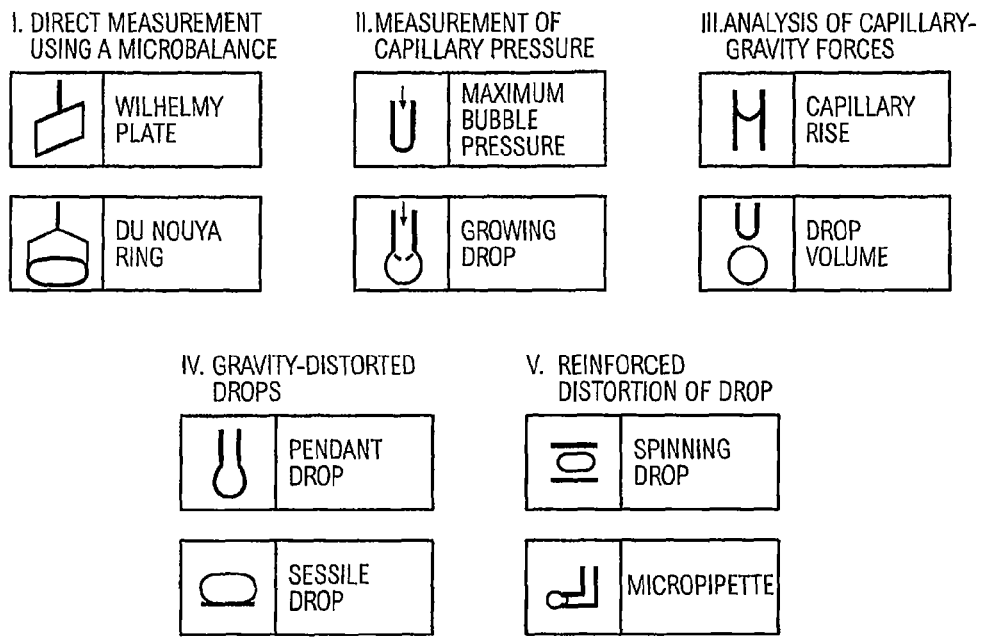
FIG. 1 is an illustration of five prior art methods for measuring of interfacial tension.
Figure 2:
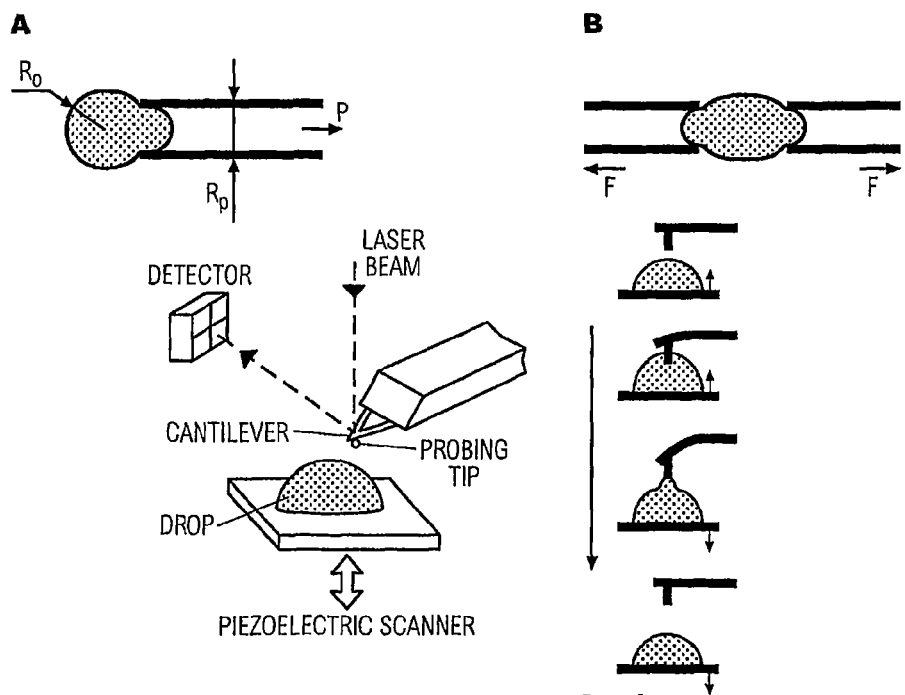
FIG. 2 is an illustration of two prior art methods of micro tensiometry.
Figure 3:
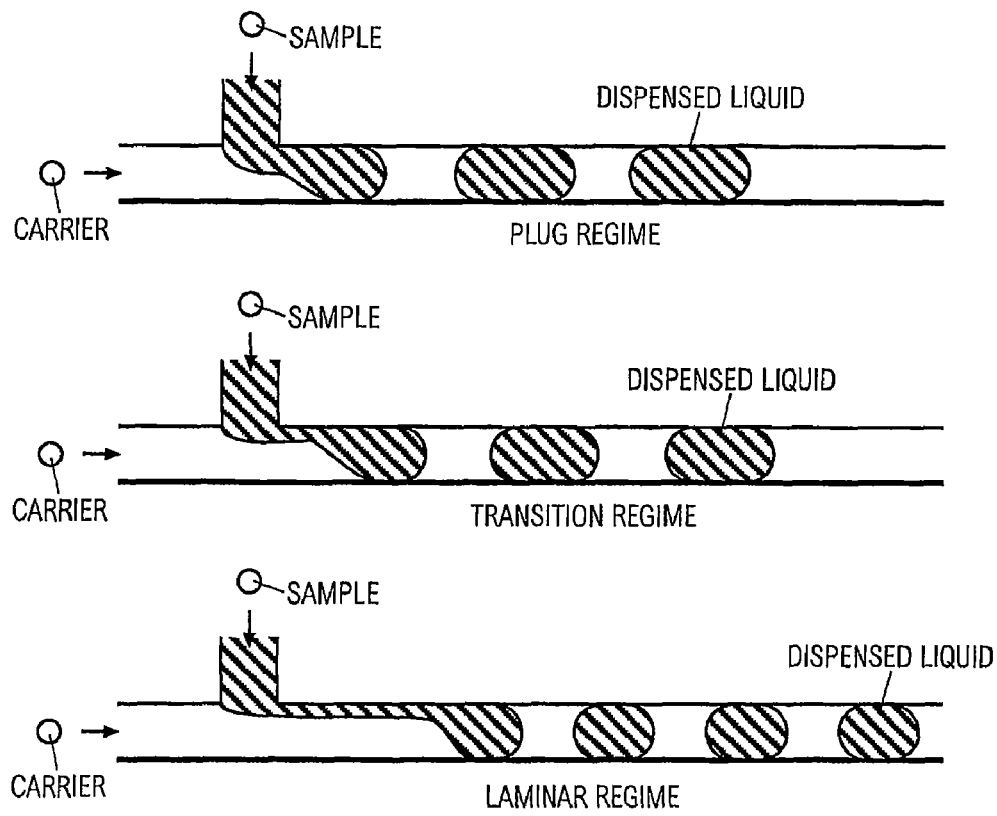
FIG. 3 is an illustration of three flow regimes of droplet formation in a microchannel.

The formation of droplets and bubbles in microchannels may be used in microreaction technology, which can be used in both the chemical industry and for biochemical analysis. Microdroplets have been used for DNA analysis, protein crystallization, analysis of human physiological fluids, and cell encapsulation. The droplets are generated and manipulated using immiscible flows. The basic configuration is shown in FIG. 3. A carrier fluid such as oil disperses a sample fluid and splits it into single droplets, the size and frequency of the droplets depending on the flow rates (represented by the Reynolds number Re) and the interfacial tension (represented by the capillary number Ca).

To refer to FIG. 3 the formation of droplet is shear-induced detachment. The balance of forces determines the final drop size at the end of the droplet growth, which is at the moment of detachment. The droplet size $V_{droplet}$ and the volumetric flow rate of the sample $\dot{Q}_{sample}$ determine the frequency of formation:

$$f = \dot{Q}_{sample}/V_{droplet} \qquad (1)$$

The following forces may contribute to the detachment balance:

Drag force on droplet:

$$F_{drag} = \frac{1}{2} C_D \rho^2 u^2 A_{droplet}^2 \qquad (2)$$

Interfacial tension force:

$$F_{interfacial} = C_S \sigma \pi D_{injection} \qquad (3)$$

Inertial force of the droplet:

$$F_{inertial} = \rho V_{droplet} \frac{du}{dt} \qquad (4)$$

Momentum force:

$$F_{momentum} = \rho \frac{\dot{Q}_{sample}}{\pi D_{injection}^2/4} \qquad (5)$$

Buoyancy force:

$$F_{buoyancy} = V_{droplet}(\rho_{carrier} - \rho)g \qquad (6)$$

NOMENCLATURES $C_D$: drag coefficient
u: carrier flow velocity and droplet velocity
$A_{droplet}$: projected area of the droplet
$V_{droplet}$: volume of the droplet
$C_S$: correction factor for surface tension force, depending on the injection angle (1 for our case of 90°)
$D_{injection}$: hydraulic diameter of the injection channel
$Q_{sample}$: volumetric flow rate of the sample
$Q_{carrier}$: volumetric flow rate of the carrier
$\alpha = Q_{sample}/Q_{carrier}$: flow rate ratio
$\rho$: density of the sample liquid
$\rho_{carrier}$: density of the carrier liquid
g: gravitational acceleration
$\sigma$: interfacial tension between sample liquid and carrier liquid In the microscale, surface effects dominate over volume effects. Thus, all forces related to droplet volume and mass such as inertial force (4), momentum force (5) and buoyancy force (6) are negligible. The force balance is reduced to the two components of drag force and interfacial force, which are both surface forces:

$$F_{drag} = F_{interfacial} \quad (7)$$

$$\frac{1}{2} C_D \rho^2 u^2 A_{droplet}^2 = C_S \sigma \pi D_{injection}$$

$$A_{droplet} = \frac{1}{\rho u} \sqrt{\frac{2C_S}{C_D} \pi D_{injection} \sigma}$$

Assuming that the droplet is a sphere with a diameter of the carrier channel $D_{carrier}$, the projected area and the volume of the droplet are:

$$A_{droplet} = \pi D_{carrier}^2 / 2 \quad (8)$$

$$V_{droplet} = \pi D_{carrier}^3 / 6$$

or $$V_{droplet} = A_{droplet} D_{carrier} / 3 \quad (9)$$

Substituting (9) in (7) results in:

$$V_{droplet} = \frac{\pi}{3} \left( \frac{C_S}{C_D} D_{injection} \frac{\sigma}{\rho_{carrier} u_{carrier}^2} \right)^{\frac{3}{2}} \quad (10)$$

Substituting (10) in (1) results in the relation between droplet formation frequency and the interfacial tension:

$$f = \frac{3\alpha D_{carrier}^2}{16(C_S D_{injection}/C_D)^{\frac{3}{2}}} \frac{\rho_{carrier}^{\frac{3}{2}} u_{carrier}^4}{\sigma^{\frac{3}{2}}} \quad (11)$$

The results show the general relations between frequency and sample flow rate ($f \sim Q_{sample}^4$) and between frequency and interfacial tension $$\left( f \sim \sigma^{-\frac{3}{2}} \right)$$

Figure 4:
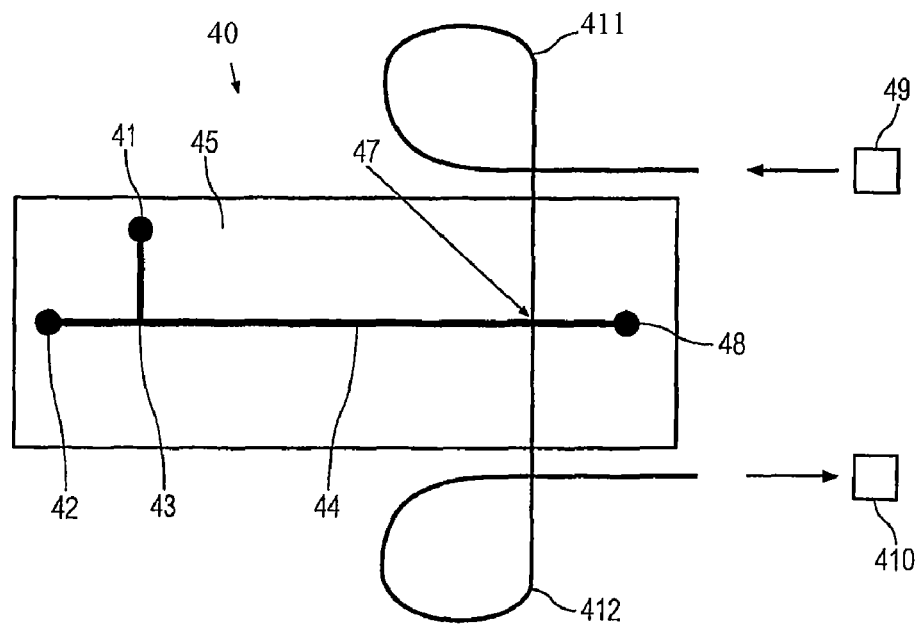
FIG. 4 is a schematic illustration of a preferred embodiment of a microfluidic device.

FIG. 4 shows the schematics of a preferred embodiment of a microfluidic device 40. The device 40 consists of two microchannels 42 joining at a T-junction 43. The channels 41, 42 are a sample inlet 41 and a carrier fluid inlet 42. After the junction 43 is a measurement channel 44. The measurement channel 44 may be of any suitable length size and shape. It may be straight (as shown), curved, serpentine or the like. The carrier fluid is fed directly into the measurement channel 44 from inlet 42, while the sample joins through the smaller inlet channel 41. Downstream of the measurement channel 44, at least one, but preferably two optical wave guides 411, 412 are positioned across the microchannel 44 for detecting the formed droplets. The optical wave guides 411, 412 are preferably optical fibers, and are axially aligned across the micro channel 44. The wave guides 411, 412 can be integrated optical guides in the chip or hybrid-assembled optical fibers. Optical fiber with a core diameter of 105 µm may be used. The optical wave signals 411, 412 are preferably at least substantially identical.

The microfluidic device 40 may be fabricated in any material: silicon, SU-8, PDMS or PMMA. The microchannels 41, 42, 44 may be machined into the substrate 45 using a $CO_2$ laser.

Figure 5A:
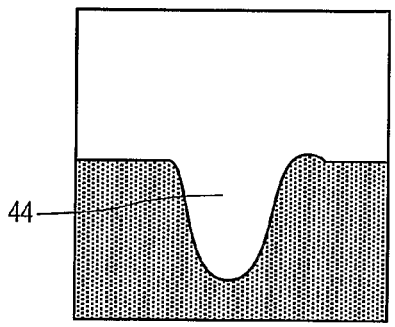
FIG. 5 is an illustration of four components of FIG. 4.
Figure 5B:
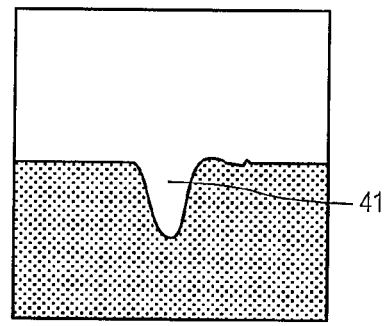
Figure 5C:
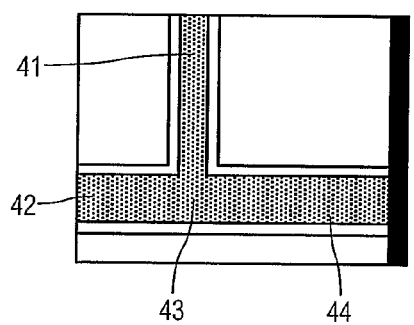
Figure 5D:
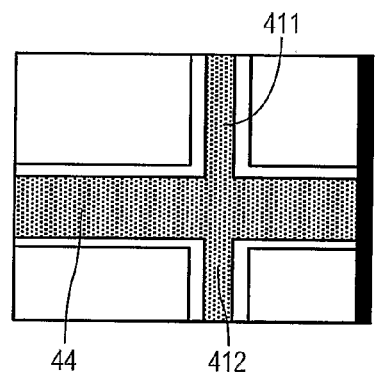

The microchannel 44 may have a typical Gaussian shape (FIG. 5(a)). Dimensions of the channel cross-section such as width and depth depend on the laser power and the laser beam speed. Different laser parameters were applied for the different channel sizes depicted in FIG. 5, where:
 (a) is the measurement channel 44,
 (b) is the sample inlet channel 41,
 (c) is the junction 43, and
 (d) is the junction 47 of the optical fiber 411, 412 and the measurement channel 44.

The two optical wave guides 411, 412 and preferably located near the outlet 48 of channel 44. If the optical wave guides 411, 412 are optical fibers, the wave guides 411, 412 may be located in guides for accurately positioning the two optical fibers 411 and 412 for optical detection. After positioning the fibers 411 and 412, the device 40 is bonded thermally at a temperature slightly above the glass temperature of PMMA. The channel guides 46 for the optical fibers 411 and 412 are sealed with adhesive to avoid leakage.

For detecting the droplets, one optical fiber 411 is positioned and aligned to a laser source 49 such, for example, a laser diode of a wavelength of, for example, 635 nm. The other optical fiber 412 is connected to a detector 410 such as, for example, an avalanche photodiode module (example: APD, C5460-01, Hamatsu, Japan). In this way it is possible to record physical characteristics of a droplet whilst still in the measurement channel 44 and as it passes between wave guides 411, 412. The characteristics include length advancing and receding edge shape, contact angle speed of velocity of movement in the measurement channel 44, and frequency of droplet formation.

The optical detection system is based on measuring the transmission of a laser beam across the measurement channel 44. The system comprises an emitting sub-system to emit a beam that illuminates the channel 44 and a light detection sub-system measuring light on a limited surface. A laser diode 49 and the optical fiber 411 may be used as the emitting sub-system, and optical fiber 412 coupled to a photo detector 410 may be used as the detecting system.

An alternative arrangement could use waveguides integrated with the fluidic device instead of optical fibers to channel the light in and out of the channel 44, allowing the distribution of light over different measurement sites.

Another version may integrate the laser diode and the photodetector directly on the microfluidic device 40 close to the measurement channel 44. The system can also include other optical elements such as a lens to improve the sensitivity of the detection by providing a reshaped beam to illuminate the measurement channel 44. Other parameter of the light beam may be measured to monitor the droplet, for example, the addition of a light polarizer would enable measurement of polarization changes.

An alternative is a capacitive detection system based on the capacitance change across the channel when a bubble/droplet is between electrodes. The detection system consists of two electrodes positioned across the channel 44. An electronic circuit such as a capacitive bridge converts the capacitance change into a voltage. The frequency, time period, and bubble/droplet shapes follow the same methods.

Example 1

A carrier oil with a viscosity of, for example, $6.52 \times 10^{-2}$ Pa·s, may be passed to channel 44 through the carrier fluid inlet 42. The sample fluid for inlet 41 may be pure DI-water (viscosity of approximately $10^{-3}$ Pa·s) or water solution of diluted surfactants. The surfactants may mixed in different volume ratios to water (0.25:80, 0.5:80, 0.75:80, 1:80, 1.25:80, 1.5:80, 1.75:80, and 2:80). Each inlet 41, 42 is driven by a syringe pump (not shown). The diameters of the syringes have a ratio of 1 to 3. Thus, the total flow rate of oil is three times that of water.

When droplets form inside the microchannel 44, the advancing and receding edge of the droplets have different contact angles and thus different radii of curvature. Using the optical detection concept described above in relation to FIGS. 4 and 5, it is possible to realize a closed loop control system with integrated micropumps for precisely generating liquid droplets or liquid plugs. This has potential in making compact droplet-based "labs on a chip".

Figure 6A:
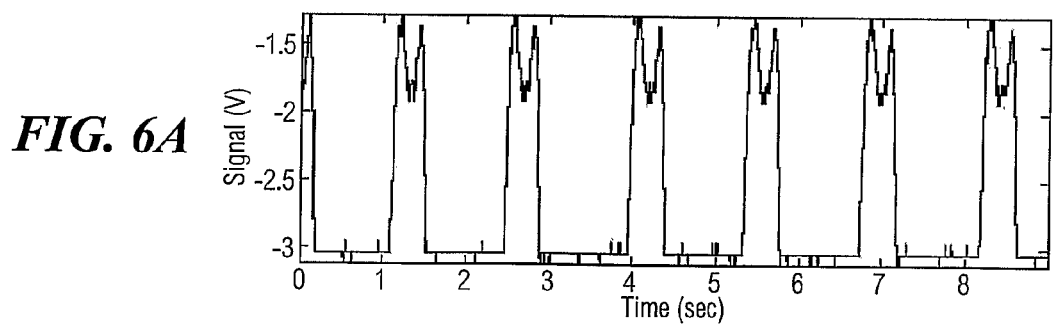
FIG. 6 is the evaluation of the optically detected signal for (a) pure water, and (b) 1 part surfactant to 80 parts water.
Figure 6B:
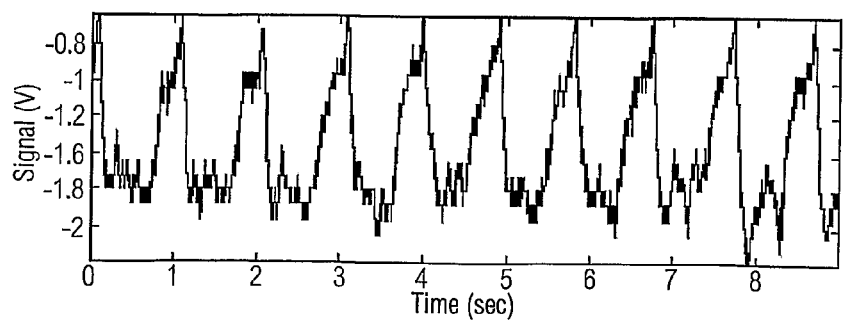

The frequency of droplet formation and the shape of the droplets depend on the flow rate of the sample, and the concentration of the surfactant. FIG. 6 shows the typical signals of the optical detection with a sample flow rate of 50 µl/hour, the detection being by use of the optical fiber detection system 49, 411, 412, 410. Decreasing the surface tension increases the formation frequency. However, the signal is distorted at high flow rates due to tiny satellite droplets.

Figure 7:
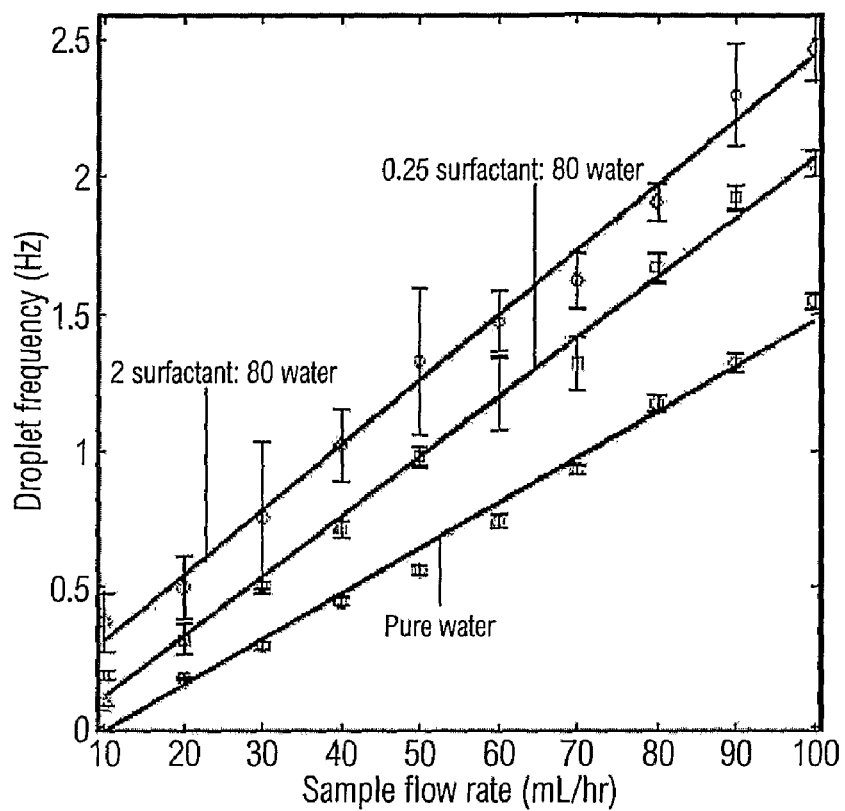
FIG. 7 is a graph of the frequency of droplet formation as a function of flow rate.

FIG. 7 shows a linear relation between the frequency of droplet formation and the sample flow rate. The error bar is larger at higher flow rate because of the noise caused by satellite droplets.

Figure 8:
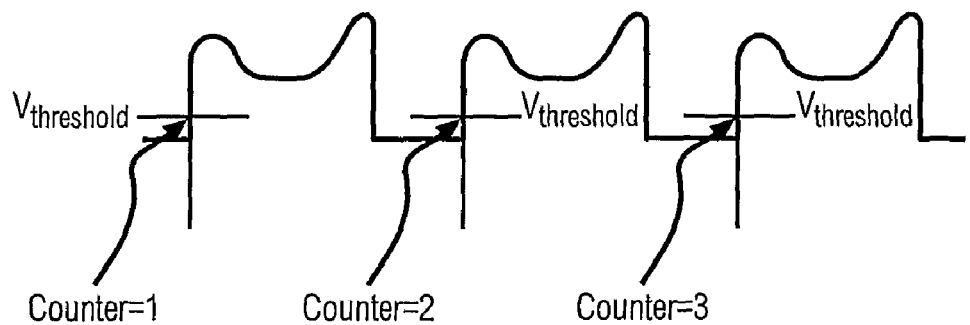
FIG. 8 is an illustration of counting the frequency of droplet formation.

As shown in FIG. 8, measuring the frequency of droplet/bubble formation is by counting the number of droplets or bubbles. If the recorded signal rises above a threshold voltage, an incremental counter increases its value. The number of droplet peaks over a fixed time represents the frequency of droplet formation.

Figure 9:
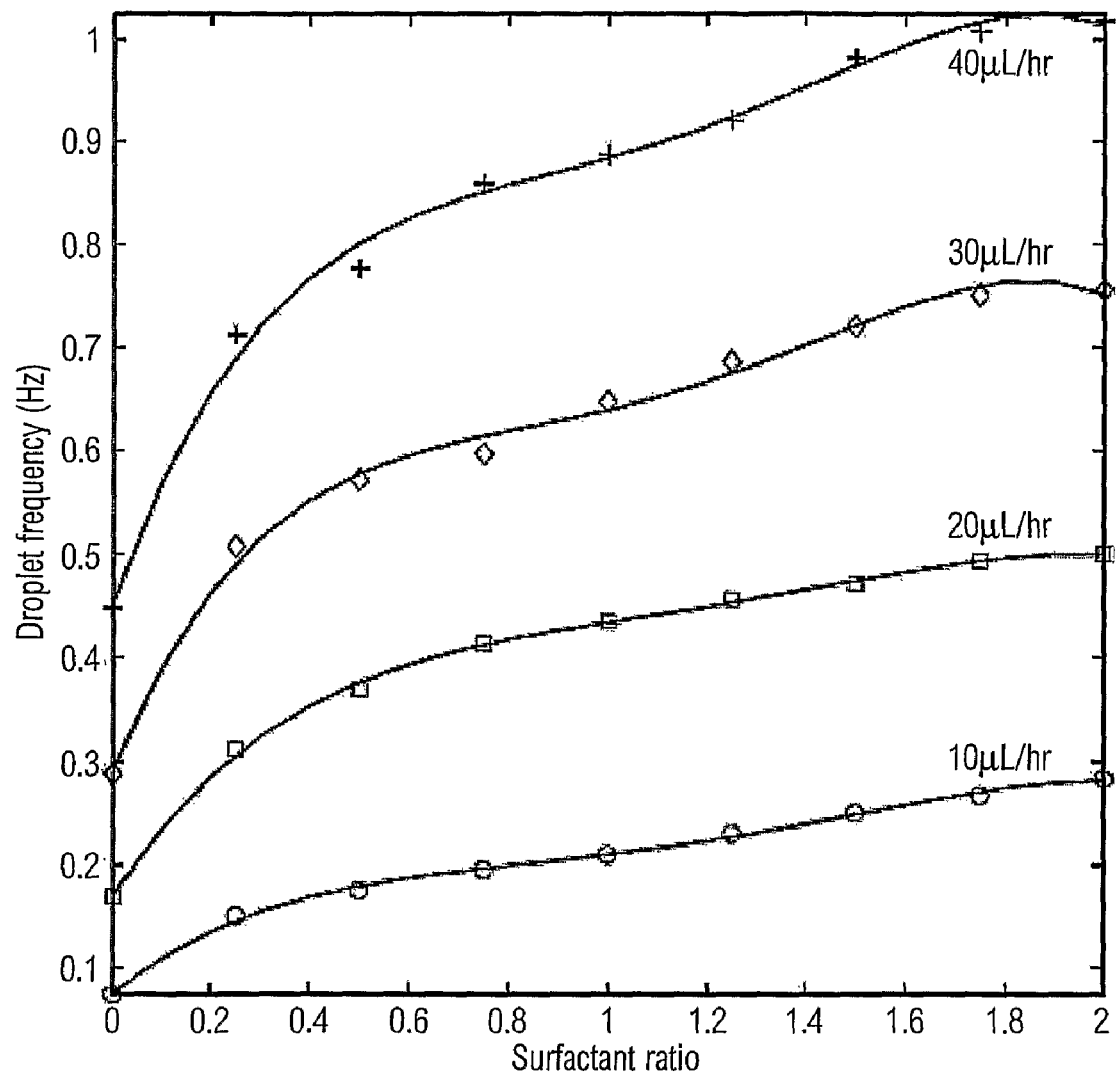
FIG. 9 is a graph of the frequency of a droplet formation as a function of surfactant concentration.

In FIG. 9, by keeping the flow rates constant, the frequency will depend only on the concentration of the surfactants or the surface tension between the sample liquid and the carrier liquid. A simple evaluation circuit can count the frequency of the optically detected signal or the time period between two signal peaks. The measured frequency or time period can be correlated with the surface tension between the two phases.

Figure 10:
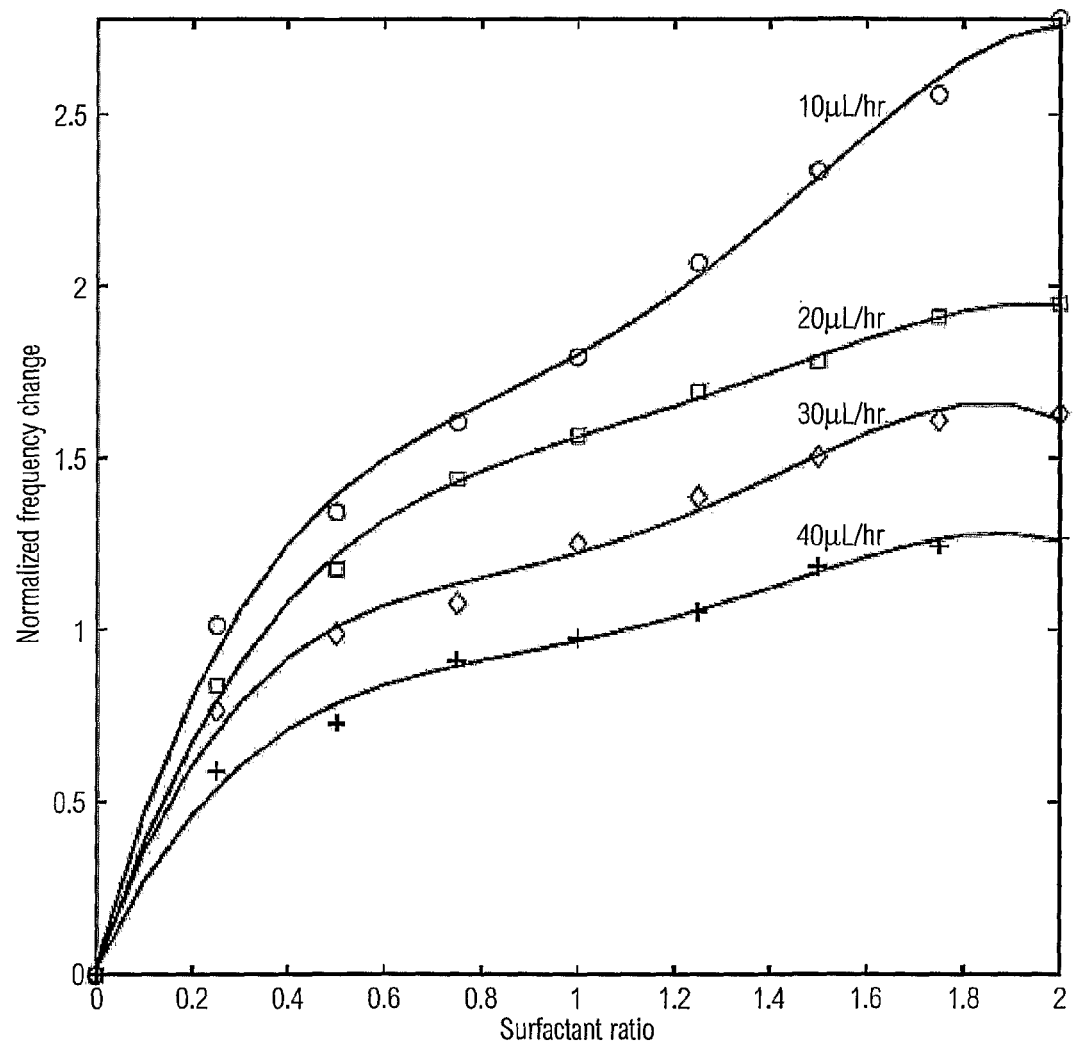
FIG. 10 is a normalized graph corresponding to that of FIG. 9.
Figure 11:
FIG. 11 illustrates the change in droplet shape at the same flow rate due to the changes in surfactant concentration.
Figure 12:
FIG. 12 illustrates the signals from the optical detection system corresponding to the droplet shapes of FIG. 11.

FIG. 10 depicts the normalized frequency change $(f-f_0)/f_0$ where $f_0$ is the frequency of droplet consisting of pure water. The curves show that the slower the flow rate, the larger is the frequency change. At lower flow rates the noise level is also lower due to a lack of satellite droplets. Small flow rates, such as those of the order of 100 nl/min, can be easily realized by different micro pump concepts, which can implemented in the same microfluidic system As shown in FIGS. 11 and 12, each peak in the detected signal represents the size and shape of each droplet. The size of droplet can be measured by the width of each peak. Since the droplet is moving, the shape of the droplet is also determined by the interfacial tension. The shape change can be easily detected by the measured signal. With a high interfacial tension, the difference between the advancing and receding sides of the droplet is minimal. The difference increases with decreasing interfacial tension. The droplet transforms into a "bullet-like" shape (see FIG. 11). The difference between the two sides can be evaluated and used as a measure of the interfacial tension. Measuring the time period of droplet/bubble formation is by determining the time between two rising edges of a signal. If the recorded signal rises above a threshold voltage, a timer (stand-alone or integrated in a microcontroller) starts counting. The timer stops counting of the signal rises above the same threshold again as is shown in, FIG. 13.

Figure 13:
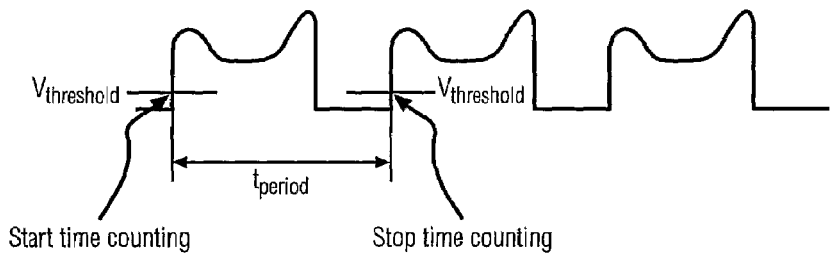
FIG. 13 illustrates the method of counting the period of the droplet/bubble formation.
Figure 14:
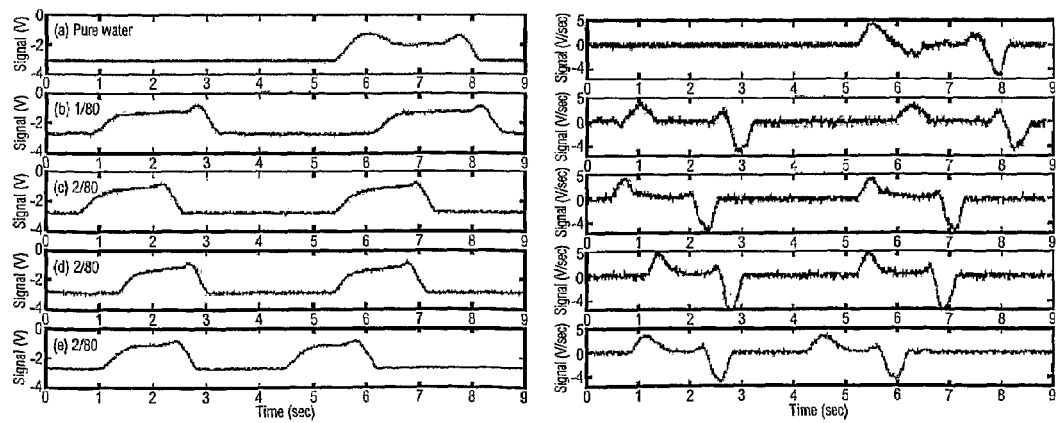
FIG. 14 are graphs of recorded signals from the optical sensor, (a) being the original time signal, and (b) being the time differential signal.

Time signals from the optical detection are fed to a digital signal processor (DSP). Next, the DSP calculates the time-differential signal of the original signal. The positive and negative peaks of the time-differential signal are detected as they represent the maximum slopes at the advancing and receding sides. The ratio or the difference between these two peaks also represents the interfacial tensions. FIG. 14 shows the typical results of this. FIG. 14(*a*) depicts the recorded time signals S(t) of droplets with different surfactant concentrations or different interfacial tensions. The signals show clearly that with decreasing surface tension the droplets are smaller and the difference between two droplets of different sizes is more easily distinguished. FIG. 14(*b*) shows time-differential signals ds(t)/dt of the data shown in FIG. 14(*a*). The positive peaks represent the receding side, while the negative peaks represent the advancing side. The difference between these two peaks is shown in FIGS. 12 and 13. The difference is a function of surfactant concentration of interfacial tension.

Figure 15:
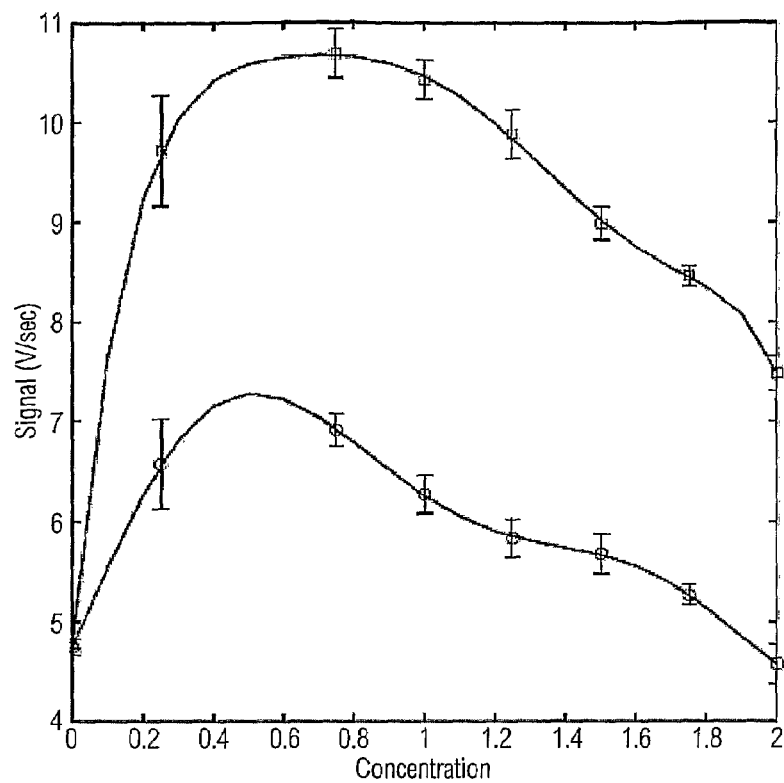
FIG. 15 is a graph of maximum values of time-differentiated signals on both sides of the droplet as a function of surfactant concentration.

FIG. 15 shows the evaluation results of the time-differential signal. The curves show the peak values of the time-differential signal versus the surfactant concentration. Unlike the characteristics of the droplet frequency shown in FIG. 9 and FIG. 10, the curve shown in FIG. 15 has a maximum. That means it is possible to have a measurement range with high sensitivity. In the graph a circle represents a receeding edge and square represents an advancing edge.

As such, there are four way of evaluating the surface tension:
- time period between two droplets;
- frequency of droplet formation;
- size of droplet; and
- difference between contact angles.

Figure 16:
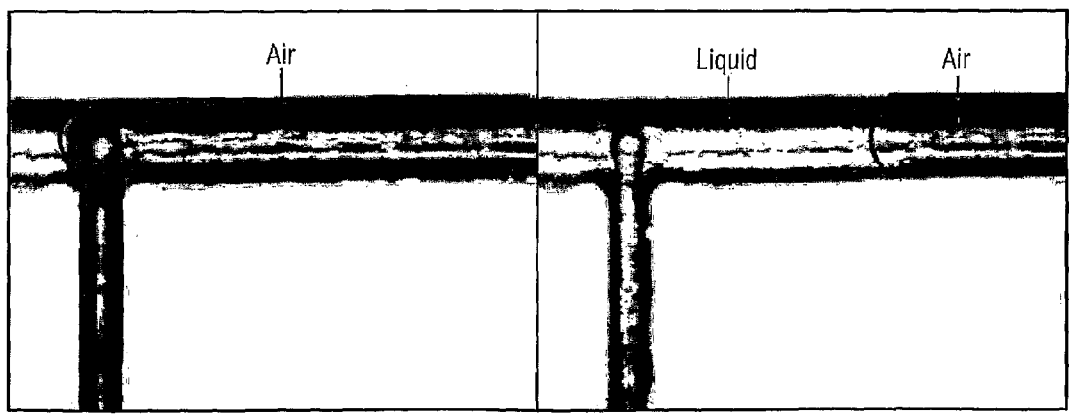
FIG. 16 is an illustration of air bubble formations inside the measurement channel.

For an air/liquid system, air is introduced into the sample inlet channel 41, while the carrier fluid channel 42 is for the sample to be measured. Both air and sample flows are driven by a syringe pump. The syringe for air may be a 0.25 mL syringe, while that for the sample may be a 1 mL syringe. The volumetric flow rate ratio between air and sample flows is kept at 1:4. FIG. 16 shows the typical bubble formation inside the microchannel 44.

Figure 17:
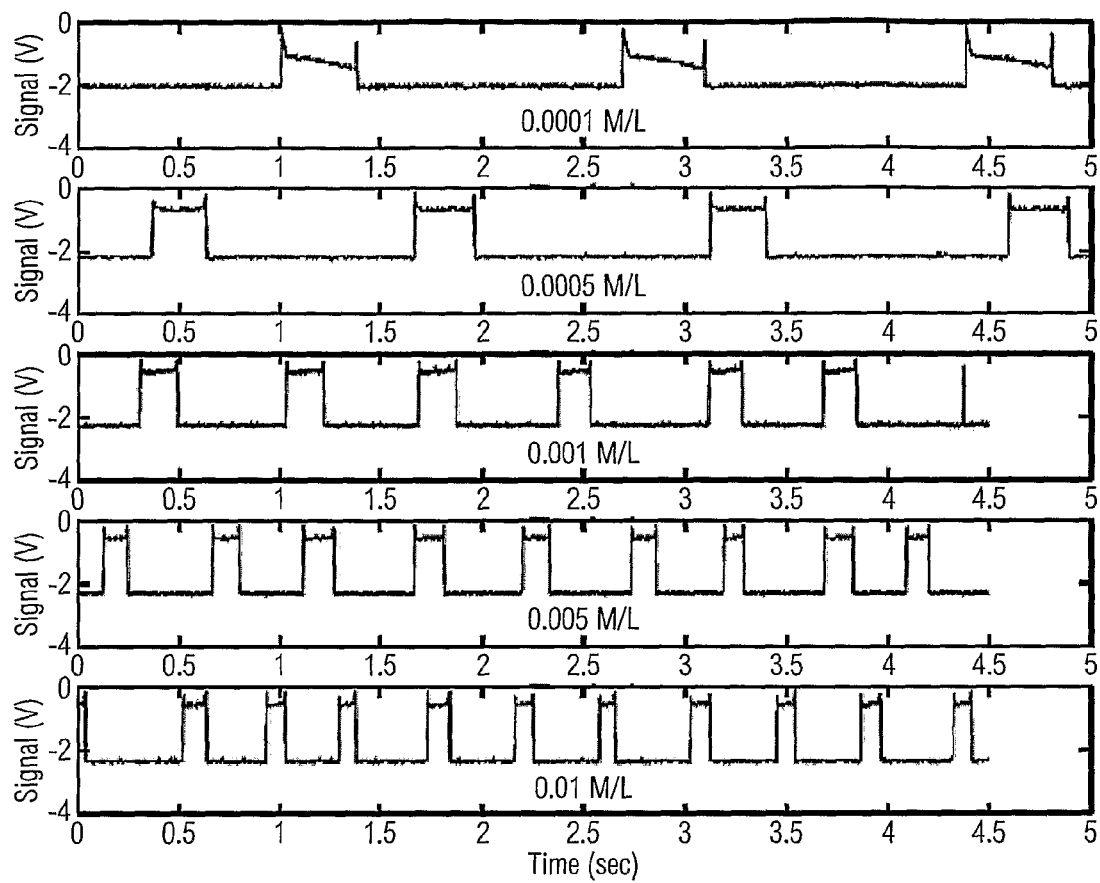
FIG. 17 shows detected signals of air bubbles at a constant flow rate with different surfactant concentrations.

FIG. 17 shows the time signal indicating the bubbles. The surfactant in use was CTAB (Cetyl Trimethyl Ammonium Bromide). Samples with different concentrations ranging from 0.0001 M/L to 0.01 M/L were tested. The surface tension of the sample decreases with the higher surfactant concentration. A higher frequency of bubble generation and a smaller bubble size can be observed.

Figure 18:
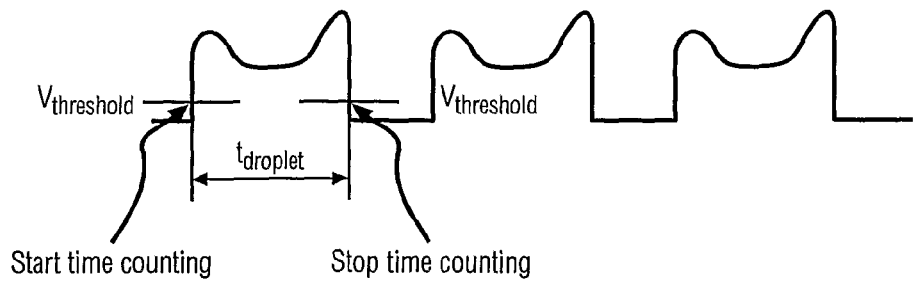
FIG. 18 illustrates the measuring of droplet/bubble size.

FIG. 18 shows that the size of droplet/bubble can be used for measuring the droplet/bubble size. If the recorded signal rises above a threshold voltage, a timer (stand-alone or integrated in a micro controller) starts counting. The timer stops counting when the signal falls under the same threshold. The counted time represents the size of the droplet/bubble.

Figure 19A:
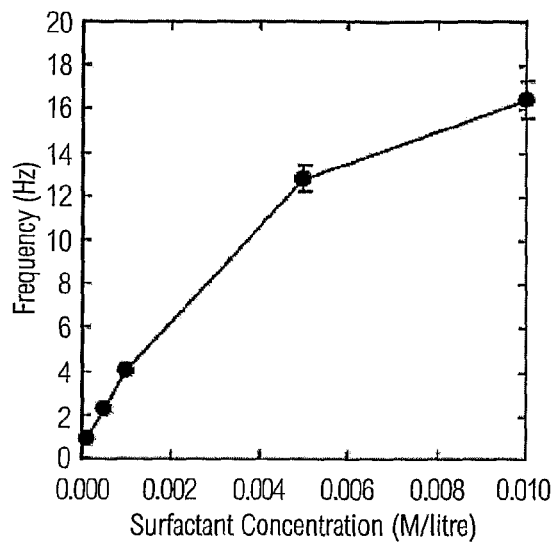
FIG. 19 is two graphs of bubble generation frequency as a function of (a) surfactant concentration, and (b) surface tension.
Figure 19B:
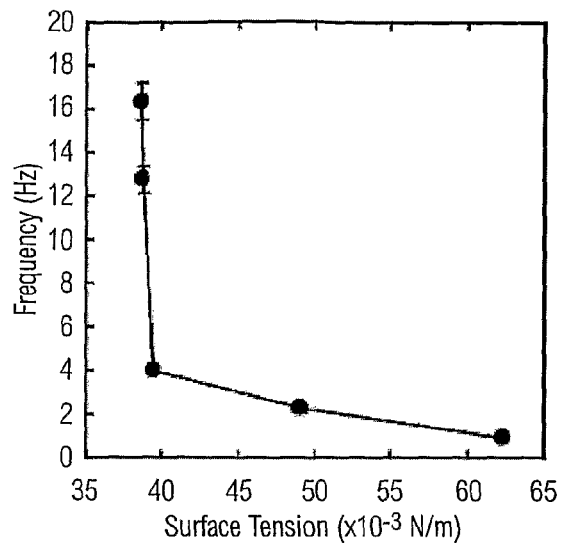

FIG. 19(a) depicts the clear dependence of bubble generation frequency on the surfactant concentration. For calibration, the surface tension of the samples was measured using a tensiometer such as, for example, FTA200 (First Ten Angstrom). The measured frequency versus the actual surface tension is depicted in FIG. 19(b). The flow rate was 3 mL/hours.

The CMC (Critical Micelle Concentration) of a surfactant can be determined by obtaining the correlation of the surface/interfacial tension versus surfactant concentration.

Figure 20A:
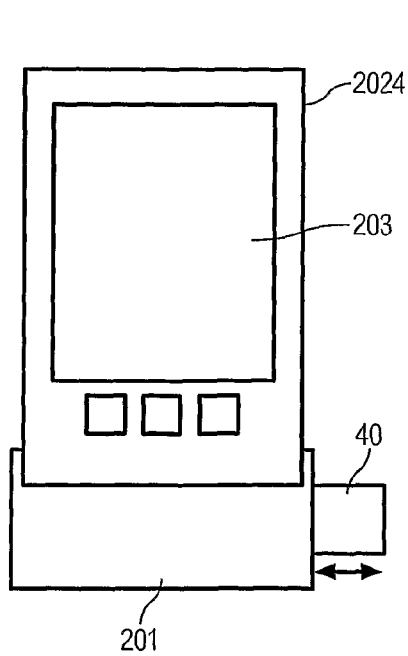
FIG. 20 illustrates two forms of handheld terminal (a) with a computing platform (handheld computer, PDA, smart phone), and (b) stand alone.
Figure 20B:
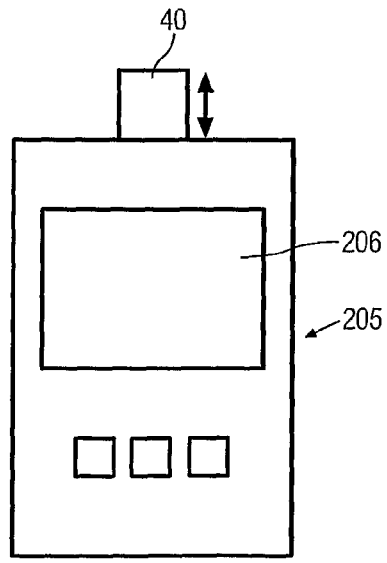

FIG. 20 illustrates the two basic concepts of a handheld tensiometer with a microfluidic sensor:
  (a) a tensiometer module 201 is attached to a hand held PC 202. The PC 202 is used as signal evaluation (look up table, polynom fitting, and so forth) and display on screen 203. The tensiometer module 201 contains all the components required and is described above. The microfluidic device 40 is inserted into the module 201, which provides fluidic, optical or electrical interconnects to the device 40.
  (b) a stand-alone device 205 with its own CPU or microcontroller, the data is displayed directly on the device LCD display 206. The insertion mechanism for the microfluidic device 40 and components are the same as in FIG. 20(a).

Figure 21A:
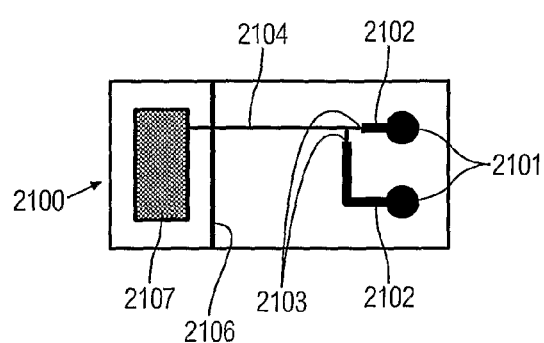
FIG. 21 illustrates four different embodiments as variants of the device of FIG. 4.

FIG. 21 depicts four different configurations of the sensor chip:

FIG. 21(a): The chip 2100 has two reservoirs 2101—one for a sample and one for the carrier. In case of a liquid/liquid system, the reservoirs 2101 are filled with the corresponding liquids. The liquid samples are first drawn into a large microchannel section 2102 due to capillary force. The samples are stopped at a capillary stop valve 2103 which is where the microchannel becomes smaller. The chip 2100 is now ready for insertion into the tensiometer module 201 or 205. The module 201, 205 provides pressure or vacuum to the reservoirs 2101 by means of an external pump and forces both liquids into the measurement channel 2104 with a constant flow rate. An optical wave guide 2105 leads light from the source 49 to the measurement channel 2104. The other optical wave 2106 guide takes the light to an optical sensor 410 in the module 201, 205. In case of impedance detection, optical guides are replaced by electrodes. In case of air/liquid system, one reservoir 2101 is left empty and, the external pump supplies air into the injection channel. The liquids are collected in a waste reservoir 2107. The chip 2100 is ready for disposal after measurement.

Figure 21B:
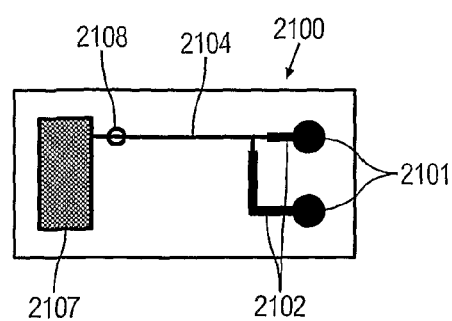

FIG. 21(b): Similar to configuration in FIG. 18(a), but there is no need for the optical wave guides 2105 and 2106. If the chip 2100 is made of a transparent material such as polymer or glass, a light source and an optical sensor 2108 can be placed directly on the chip on opposite sides of channel 2104.

Figure 21C:
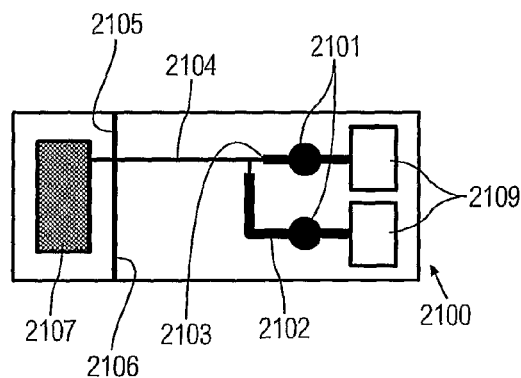

FIG. 21(c): Similar to configuration in FIG. 21(a), but two integrated micropumps 2109 are used for sample delivery. The micropumps 2109 may be checkvalve pumps, peristaltic pumps, valveless pumps, centrifugal pumps, electroosmotic pump, electrohydrodynamic pump and so forth. The pumps 2109 may be equipped with flow sensors for keeping the flow rate constant. Control signals for the pumps 2109 come from the tensiometer module 201, 205.

Figure 21D:
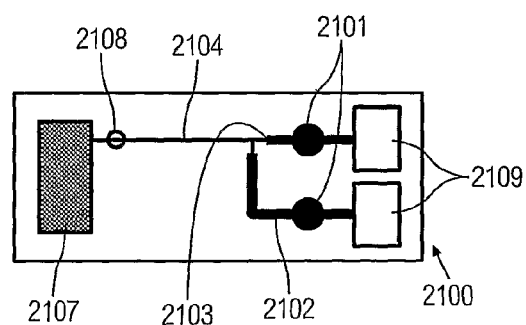

FIG. 21(d) Similar to configuration in FIG. 21(b), but the chip 2100 has two integrated micropumps 2109 in the same manner as FIG. 21(c).

Figure 22:
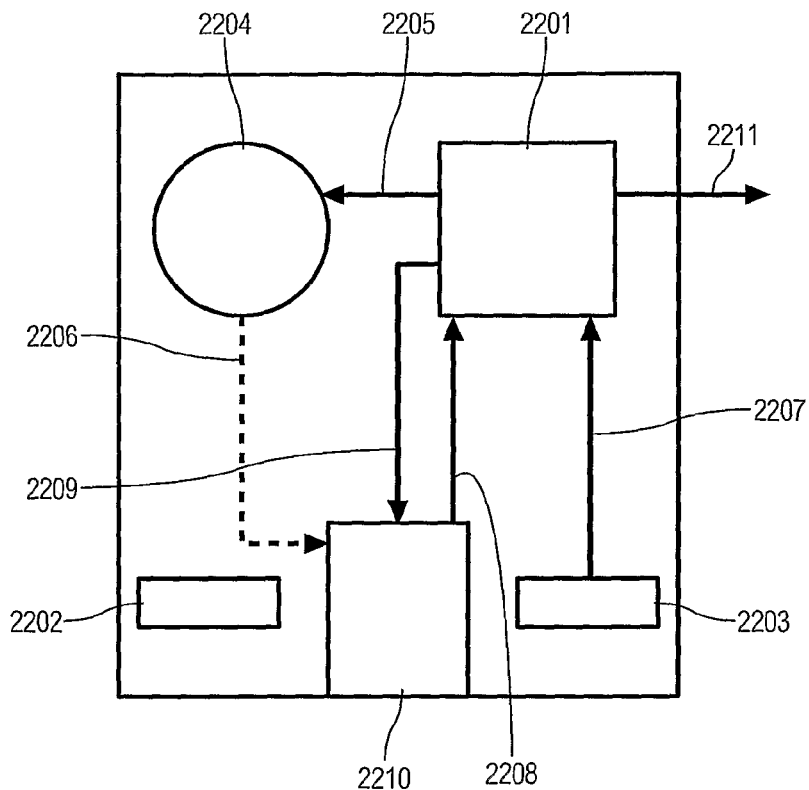
FIG. 22 illustrates an embodiment of a tensiometer module for FIG. 21.

FIG. 22 shows a tensiometer module 201, 205. The central component of this module 201, 205 is a microcontroller or a digital signal processor.

In case of optical detection, the module provides a light source 2202 and an optical sensor 2203.

Control signals 2205 for the pump 2204 are from microcontroller 2201. Signals 2207 from the optical sensor 2203 (or signals 2208 from the capacitive sensor) are evaluated in the microcontroller 2201. When these integrated micropumps 2109, signals 2209 for the micropump 2109 are from the microprocessor.

In case of external pumping, the modules provide a mini pump 2204 for pressure/vacuum supply to the sensor chip. The mini pump 2204 may be in the form of conventional check-valve pump, or a small syringe pump driven by a stepper motor. Before measurement, the syringes would be withdrawn to a charging position.

An insertion slot 2210 is provided for the chip 2100, the slot 2100 having fluidic, optical and/or an electrical inter connects. Measurement results 2211 are sent from microcontroller 2201 to screens 203, 206.

Figure 23:
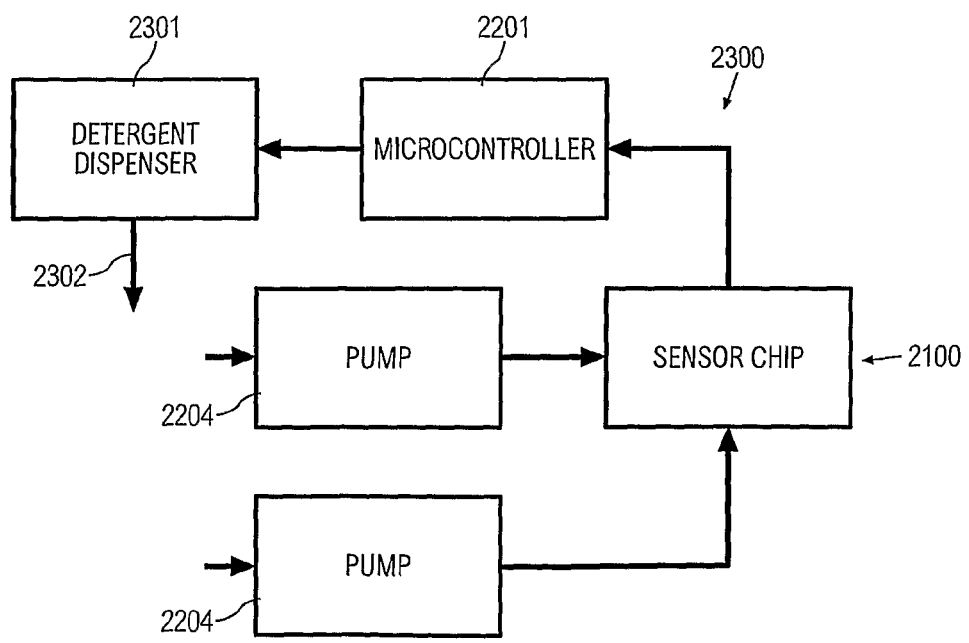
FIG. 23 illustrates an embodiment for use in a detergent dispenser.

FIG. 23 shows the concept of a close-loop controlled detergent dispenser 2300 with a sensor 2100 and two pumps 2204, one for air and the other for washing liquids. The sensor 2100 provides information about surface tension or CMC (Critical Micelle Concentration) of the washing liquid. The microcontroller 2201 uses this information to control the detergent dispenser 2201. This concept can be integrated in a commercial washing machine to save detergent 2302 and protect the environment.

The preferred embodiments allow the fast determination of dynamic interfacial tension of a liquid/liquid system, or a gas/liquid system. The chip 40 can be designed for disposable use and easily be integrated in a more complex microfluidic system. Besides the advantage of a fast analysis, a handheld measurement device with this sensor has the potential to replace all current desktop system for determining surface tension in, for example, the petroleum industry. Surface tension, contact angle, and CMC (Critical Micelle Concentration) of a surfactant play an important role in the displacement of oil from the pore spaces of sedimentary rocks, in wetting and dewetting of oil from sand grains, in dewatering in refinery plants, and separation and flotation in oil recovery. Feedback-controlled detergent dosing for washing machines is another use.

Whilst there has been described in the foregoing description preferred embodiments of the present invention, it will be understood by those skilled in the technology concerned that many variations or modifications in details of design or construction may be made without departing from the present invention.

The invention claimed is:
1. A microfluidic system for interfacial tension measurement,
  the system comprising:
    a first inlet channel for a first fluid;
    a second inlet channel for a second fluid;
    a measurement channel intersecting with both the first inlet channel and the second inlet channel whereby an intersection of the first inlet channel, the second inlet channel and the measurement channel form a T-junction;
    an optical signal source system for transmitting a signal from a signal emitter;

an optical signal detection system for receiving the signal from the signal source system; and a processing system configured to determine interfacial tension of at least one droplet or bubble in the measurement channel based, at least in part, on output from the optical signal detection system;

wherein the optical signal source system and the optical signal detection system are axially aligned on opposite sides of the measurement channel such that the signal from the optical signal source system transmitted to the measurement channel crosses the measurement channel substantially perpendicular to a fluid flow direction of a fluid flowing in the measurement channel during use.

2. A microfluidic system as claimed in claim 1, wherein the first fluid is air.

3. A microfluidic system as claimed in claim 1, wherein the signal emitter is a laser emitter, and wherein the optical signal detection system comprises a signal detector which is an optical sensor.

4. A microfluidic system as claimed in claim 1, further comprising a tensiometer module comprising a receptor, the receptor comprising electrical and optical connections.

5. A microfluidic system as claimed in claim 1, wherein the optical signal source system and the optical signal detection system are configured to evaluate at least one physical characteristic of the at least one droplet or bubble disposed in the measurement channel.

6. A microfluidic system as claimed in claim 1, wherein the processing system includes at least one of a digital signal processor and a microcontroller, the at least one of the digital signal processor and the microcontroller communicatively coupled to the optical signal detection system and configured to calculate a time-differential signal based on signals from the optical signal detection system, determine positive peaks and negative peaks of the time-differential signal, and determine a ratio or a difference between the positive peaks and the negative peaks.

7. A microfluidic system as claimed in claim 1, wherein the first inlet channel, the second inlet channel and the measurement channel are in a substrate.

8. A microfluidic system as claimed in claim 7 wherein the substrate is transparent.

9. A microfluidic system as claimed in claim 8, wherein the optical signal detection system comprises an optical sensor.

10. A microfluidic system as claimed in claim 1, wherein the signal source system comprises a source wave guide, and the signal detection system comprises a detection wave guide.

11. A microfluidic system as claimed in claim 10, wherein the source wave guide is a source optical fiber, and the detection wave guide is a detection optical fiber.

12. A microfluidic system as claimed in claim 10, wherein the source wave guide and the detection waive guide are in a substrate.

13. A microfluidic system as claimed in claim 1, further comprising a first fluid reservoir operatively connected to the first inlet channel, a second fluid reservoir operatively connected to the second inlet channel, and a waste reservoir operatively connected to an outlet end of the measurement channel.

14. A microfluidic system as claimed in claim 13, further comprising a first pump operatively connected to the first fluid reservoir for forcing the first fluid into the first inlet channel and the measurement channel; and a second pump operatively connected to the second fluid reservoir for forcing the second fluid into the second inlet channel and the measurement channel.

15. A microfluidic system as claimed in claim 1, wherein a straight section of the measurement channel is between the optical signal detection system and the optical signal source system, the straight section extends through and away from a signal path from the optical signal source system to the optical signal detection system.

16. A microfluidic sensor as claimed in claim 15, wherein the straight section of the measurement channel defines a fluid path, the entire fluid path is substantially perpendicular to the signal path.

17. A method for measuring physical characteristics of at least one droplet or bubble of a first fluid in a measurement channel of a microfluidic sensor for interfacial tension measurement, the method comprising:

(a) forcing a first fluid along a first inlet and into the measurement channel;

(b) forcing a second fluid along a second inlet and into the measurement channel to form the at least one droplet or bubble, wherein the first inlet, the second inlet and the measurement channel intersect at and form a T-junction and wherein the first fluid and the second fluid are immiscible;

(c) using an optical signal source system to provide a source signal and an optical signal detection system to detect the source signal; and (d) determining interfacial tension of at least one droplet or bubble of the first fluid by using the signal source system and the signal detection system.

18. A method as claimed in claim 17, wherein the first fluid is air and the droplets are air bubbles.

19. A method as claimed in claim 17, wherein the signal source system and the signal detection system are axially aligned on opposite sides of and intersect with the measurement channel.

20. A method as claimed in claim 17, wherein the optical signal source system comprises a laser emitter, and wherein the optical signal detection system comprises an optical sensor.

21. A method as claimed in claim 17, further comprising evaluating at least one physical characteristic of at least one droplet or bubble in the measurement channel using the optical signal source system and the optical signal detection system.

22. A method as claimed in claim 17, wherein the first inlet channel, the second inlet channel and the measurement channel are in a substrate.

23. A method as claimed in claim 22, wherein the substrate is transparent.

24. A method as claimed in claim 23, wherein the signal source system comprises a light emitter and the signal detection system comprises an optical sensor.

25. A method as claimed in claim 17, wherein the signal source system comprises a source wave guide, the source signal is light, and the signal detection system comprises a detection wave guide.

26. A method as claimed in claim 25, wherein the source wave guide is a source optical fibre, and the detection wave guide is a detection optical fibre.

27. A method as claimed in claim 25, wherein the source wave guide and the detection waive guide are in a substrate.

28. A method as claimed in claim 17 further comprising a first fluid reservoir operatively connected to the first inlet, a second fluid reservoir operatively connected to the second inlet, and a waste reservoir operatively connected to an outlet end of the measurement channel.

29. A method as claimed in claim 28, further comprising using a first pump connected to the first fluid reservoir to force the first fluid into the first inlet and the measurement channel; and using a second pump connected to the second fluid reservoir to force the second fluid into the second inlet and the measurement channel.

30. A computing apparatus comprising the microfluidic system as claimed in claim 4, and a screen.

31. The computing apparatus as claimed in claim 30, wherein the tensiometer module is removable.

* * * * *